United States Patent [19]

Imbert

[11] Patent Number: 5,601,077
[45] Date of Patent: Feb. 11, 1997

[54] NASAL SYRINGE SPRAYER WITH REMOVABLE DOSE LIMITING STRUCTURE

[75] Inventor: Claude Imbert, La Tronche, France

[73] Assignee: Becton, Dickinson and Company, Franklin Lakes, N.J.

[21] Appl. No.: 742,675

[22] Filed: Aug. 7, 1991

[51] Int. Cl.⁶ .......................... A61M 11/00; A61M 5/315; A61M 5/31; A62B 7/00
[52] U.S. Cl. ............... 128/200.14; 128/207.18; 128/200.22; 604/239; 604/236; 604/237
[58] Field of Search ............ 128/200.14, 200.19, 128/200.24, 203.12, 207.18; 604/54, 68, 70–72, 236, 237, 246–249, 294, 296, 310, 311, 239

[56] References Cited

U.S. PATENT DOCUMENTS

| | | | |
|---|---|---|---|
| 3,373,743 | 3/1968 | Saffir | 604/237 |
| 3,502,078 | 3/1970 | Hill et al. | 128/232 |
| 3,874,380 | 4/1975 | Baum | 128/206 |
| 3,874,381 | 4/1975 | Baum | 128/206 |
| 4,112,924 | 9/1978 | Ferrara et al. | 604/237 |
| 4,493,348 | 1/1985 | Lemmons | 604/54 |
| 4,767,416 | 8/1988 | Wolf et al. | 604/239 |
| 4,919,167 | 4/1990 | Manska | 604/247 |
| 4,923,448 | 5/1990 | Ennis, III | 604/239 |
| 5,098,405 | 3/1992 | Peterson et al. | 604/247 |

FOREIGN PATENT DOCUMENTS

| | | |
|---|---|---|
| 0334349 | 3/1989 | European Pat. Off. . |
| 2635084 | 8/1988 | France . |

*Primary Examiner*—Kimberly L. Asher
*Attorney, Agent, or Firm*—John L. Voellmicke

[57] ABSTRACT

A syringe nasal sprayer includes an elongate barrel having an open proximal end, a chamber for retaining fluid and a tip portion extending from a distal end of the barrel having a passageway therethrough communicating with the chamber. A stopper is slidably positioned in fluid-tight engagement inside the barrel. An elongate plunger rod projects proximally from the stopper and extends outwardly from the open proximal end of the barrel. A spray nozzle extends outwardly from the tip portion and includes a conduit therethrough in fluid communication with the passageway. A distal end of the nozzle includes a spray aperture in fluid communication with the conduit. The nozzle also includes an internal valve for allowing liquid under pressure in the chamber to flow distally through the conduit and through the aperture while preventing unpressurized liquid in the chamber from flowing through the aperture.

13 Claims, 5 Drawing Sheets

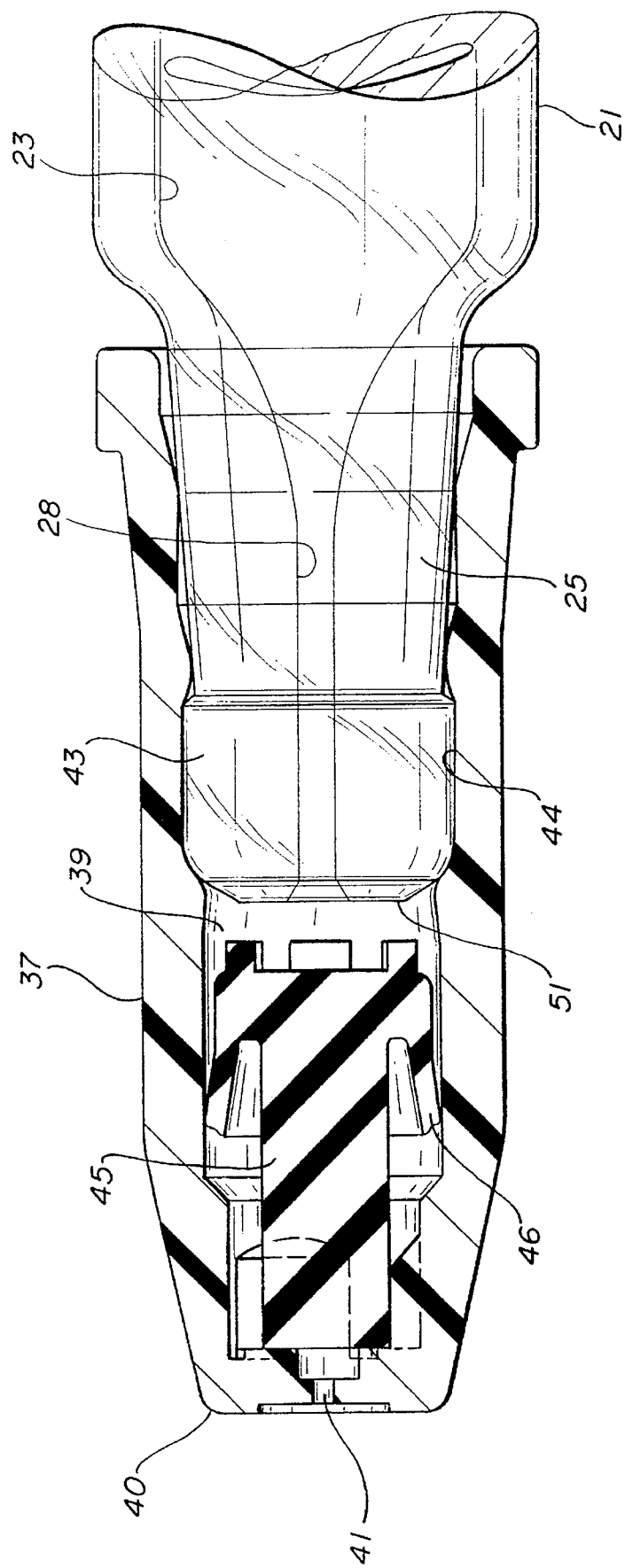

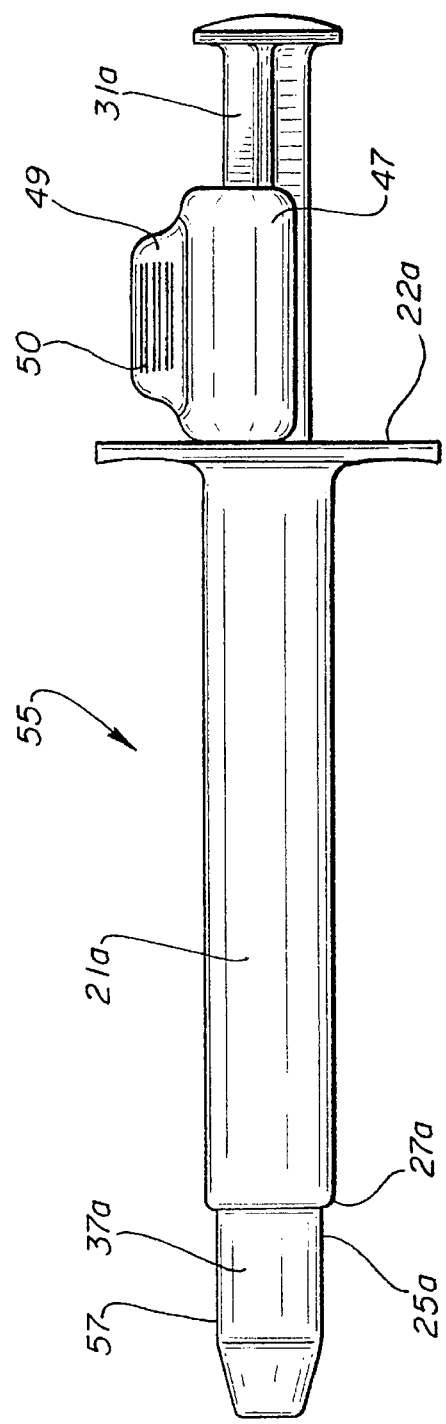
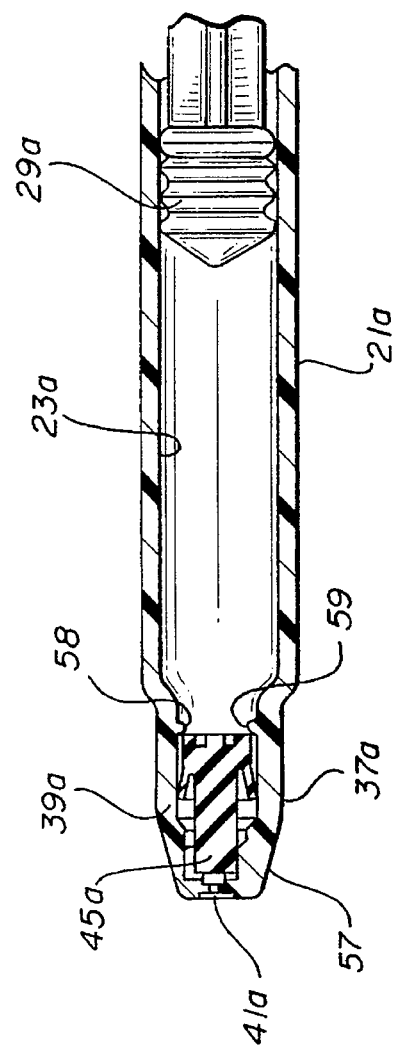
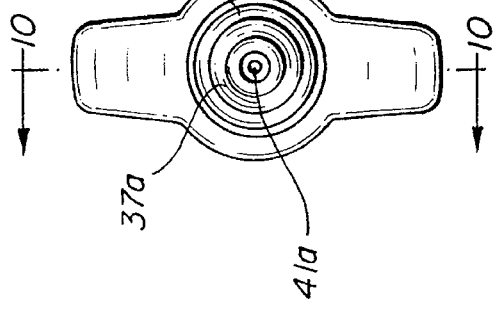

NASAL SYRINGE SPRAYER WITH REMOVABLE DOSE LIMITING STRUCTURE

BACKGROUND OF THE INVENTION

1. Field of the Invention.

The present invention relates to syringes and more particularly concerns syringe assemblies capable of spraying liquid.

2. Description of Related Information.

Many injectable medications are packaged and distributed in hypodermic syringes that will eventually be used to administer the medication to the patient. Prefilled syringes are available from pharmaceutical manufacturers, and syringes are frequently prefilled in hospital pharmacies. In both instances, the prefilled syringe is subject to a variety of environmental challenges due to storage, shipping and/or handling before medication is administered to the patient. Accordingly, the contents of the syringe must be sealed to preserve their stability and/or sterility.

In some medical procedures, it is necessary or desirable to apply therapeutic liquids to a wound or surgical site by spraying the liquid onto the affected area. It is also sometimes desirable to administer the therapeutic liquid spray to the eye, ear, nose or throat of a patient rather than delivering the therapeutic liquid though a hypodermic needle. A growing area of activity involves the spraying of therapeutic liquids into the nasal cavity of a patient. This delivery route eliminates the need for puncturing the patient's skin with a sharp hypodermic needle and eliminates the possibility of other health care workers being exposed to a sharp non-sterile or contaminated hypodermic needle.

The syringe is the low cost, efficient, sterile instrument of choice for delivering liquid medication through a hypodermic needle. The hypodermic syringe can also be an excellent storage device for medication placed in it by a pharmaceutical manufacturer or hospital pharmacy. The delivery of therapeutic liquid via spray, through the nasal passageway, is a preferred method for the delivery of certain therapeutic liquids under certain conditions.

The art has not taught a device for the intranasal delivery of therapeutic liquid which incorporates the significant cost, performance and storage advantages of a prefilled hypodermic syringe. For example, U.S. Pat. Nos. 3,874,380 and 3,874,381 to Baum teach a dual nozzle intranasal delivery device which uses a hypodermic syringe in a very complicated set up involving a medication vial and a hypodermic needle and complex passageways for converting a stream of liquid from a hypodermic syringe into two separate passages leading to adjacent parallel spray nozzles.

U.S. Pat. No. 3,502,078 to Hill et al. teaches a dual-tipped nasal syringe and aspirating device which includes dual syringe bulbs connected to parallel tubes leading to dual nostril engaging tips. Although the device of Hill et al. appears to be costly to manufacture and may have shortcomings with respect to its capability to delivering all of the medication contained therein, it does offer an advantage over Baum's device in that both nostrils will receive no more than the amount of liquid medication in each side of the device. Accordingly, an equal dose volume can be delivered to each nostril.

U.S. Pat. No. 4,923,448 to Ennis, III teaches a syringe with spray nozzle tip for discharging the liquid contents of the syringe in a spray. The syringe of Ennis, III is an improvement over prior art devices in that it attempts to combine the efficiency of a syringe with a spray nozzle. However, the syringe of Ennis, III due to its structure cannot be used to store medication and should be filled at the time of use. It appears that medication in the barrel of the Ennis, III syringe can drain out of the spray aperture since no structure either blocks this possible flow or protects the device from outside contaminants. Providing a protection cap over the tip of the Ennis, III syringe would apparently still allow an amount of the liquid to pass through the aperture into the protective cap where it cannot be delivered to the patient. A similar syringe device is taught by Wolf et al. in U.S. Pat. No. 4,767,416 except the spray nozzle of Wolf et. al. is a separate attachment which may be added to the syringe at the time of use. Accordingly, the syringe may be used as a storage device. However, the use of such a device requires additional components, procedures and opportunities for contamination and additional cost because the syringe must be assembled with the sprayer at the time of use. The assembly of the syringe of Wolf can also present a safety problem because the locking luer tip of the syringe can readily accept a hypodermic needle and allow injection of a medication formulated for spray application only. Also, neither Wolf et al. nor Ennis, III provide any structure to control the amount of medication delivered to each nostril. If it is preferable to split the dose between the nostrils the operator of these syringes must rely on guess work or volume measuring indicia on the syringe barrel if such indicia exists.

European Patent Application No. 0 334 349 teaches a device for a dosage dispensing of a liquid medicine which provides structure for controlling the dose so that equal or predetermined amounts may be delivered with each stroke of the syringe. However, the device of the '349 patent application is extremely complex and involves covering structure over the syringe which appears to be substantially more expensive and difficult to assemble, fill and use.

The prior art also includes commercially available over-the-counter nose drop spray pump and reservoir assemblies. In use these devices have a spray tip which is placed in the nostril and the pump is manually cycled to deliver medication. These devices are not suitable for many forms of therapy because the dose cannot be accurately controlled at the reservoir which may contain 20 or more doses that could be delivered at one time. Accordingly, these spray pump/reservoirs can be dangerous because of their ability to deliver substantial overdoses.

While the art has recognized the use of hypodermic syringes for the efficient storage and delivery of liquid medication and that the preferred delivery of some medications in the form of a spray to areas of the body such as the nasal cavity, there is still a need for a simple prefillable medication delivery device which combines all of the delivery and storage advantages of a hypodermic syringe with the ability to deliver medication in the form of a spray without complex adapters or assembly procedures at the time of use wherein said delivery device can include single use features to help prevent refilling and reuse. In the case of nasal sprayers there is also a need to control the amount of medication delivered to each nostril and to assure that only a single dose would be delivered.

SUMMARY OF THE INVENTION

The syringe sprayer of the present invention comprises an elongate barrel having an open proximal end, a chamber for retaining liquid and a tip portion extending from a distal end of the barrel having a passageway therethrough communicating with the chamber. A stopper is slidably positioned in fluid-tight engagement inside the barrel. An elongate plunger rod projects proximally from the stopper and extends outwardly from the open proximal end of the barrel. The plunger rod includes a radially extending flange on its proximal end. A spray nozzle extends outwardly from the tip portion of the barrel and includes a conduit therethrough in fluid communication with the passageway of the tip portion of the barrel. A distal end of the nozzle includes a spray aperture in fluid communication with the conduit. A spray nozzle includes an internal flexible valve which allows liquid under pressure in the chamber to flow distally through the conduit and the aperture while preventing unpressurized liquid in the chamber from flowing through the aperture. The internal valve is configured so that it also functions as a one-way valve for preventing liquid flow through the conduit in a proximal direction toward the chamber of the barrel. This embodiment also includes a dose limiting housing for preventing delivery of a pre-determined amount of liquid in the chamber through the passageway by limiting the distal motion of the plunger rod with respect to the barrel. The dose limiting housing also includes an override feature for allowing delivery of all of the liquid in the chamber. In this embodiment, the override feature allows the removal of the housing from the syringe nasal sprayer.

In another embodiment of the present invention a syringe sprayer comprises an elongate barrel having an open proximal end, a chamber for retaining fluid and a tip portion extending from the distal end of the barrel having a passageway therethrough communicating with the chamber. A stopper is slidably positioned in fluid-tight engagement inside the barrel. An elongate plunger rod projects proximally from the stopper and extends outwardly from the proximal end of the barrel. A spray nozzle extends outwardly from the tip portion of the barrel and includes a conduit therethrough in fluid communication with the passageway. A distal end of the spray nozzle includes a spray aperture in fluid communication with the conduit. The nozzle also includes an internal valve for allowing liquid under pressure in the chamber to flow distally through the conduit and aperture while preventing unpressurized liquid in the chamber from flowing through the aperture.

BRIEF DESCRIPTION OF THE DRAWINGS

FIG. 7 is an enlarged cross-sectional view of the spray nozzle of the syringe nasal sprayer illustrating a two-component spray nozzle assembly having one-way valve features;

FIG. 8 is a side elevational view of an alternative embodiment of the syringe nasal sprayer of the present invention;

FIG. 9 is a side elevational view of the syringe nasal sprayer of FIG. 8 as viewed from the distal end; and FIG. 10 is a partial cross-sectional view of the distal end of the syringe nasal sprayer of FIG. 9 taken along line 10—10.

DETAILED DESCRIPTION

Figure 1:
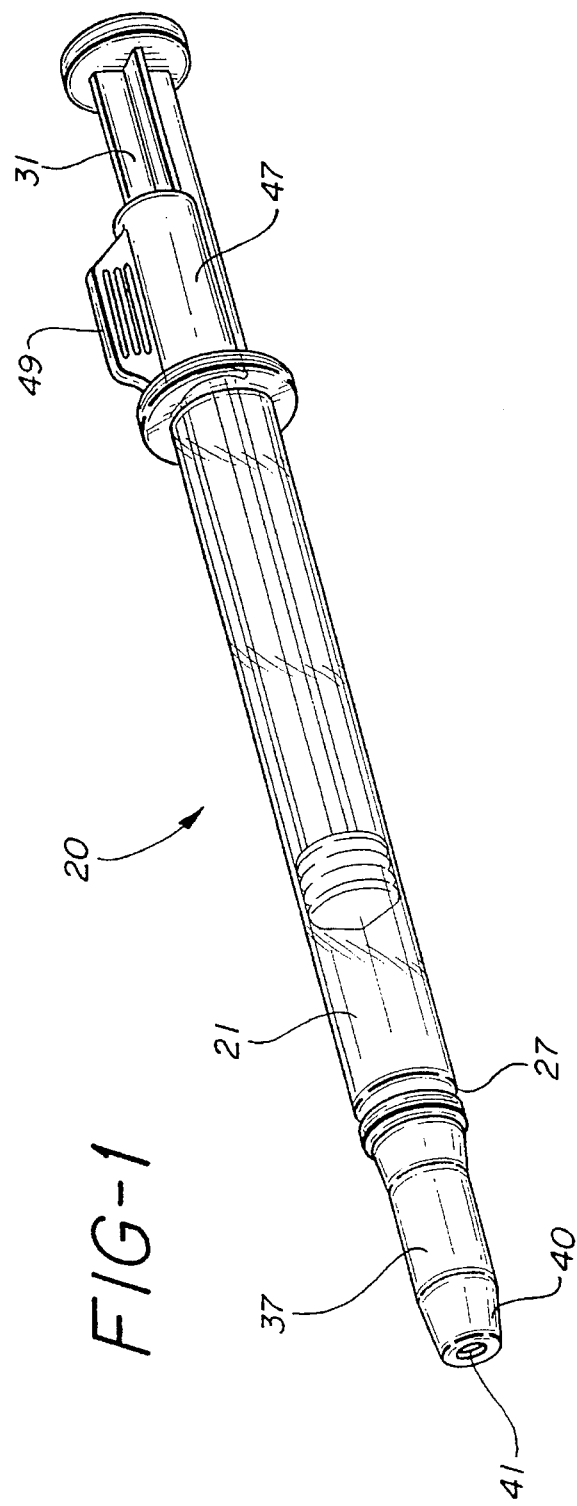
FIG. 1 is a perspective view of the syringe nasal sprayer of the present invention.
Figure 2:
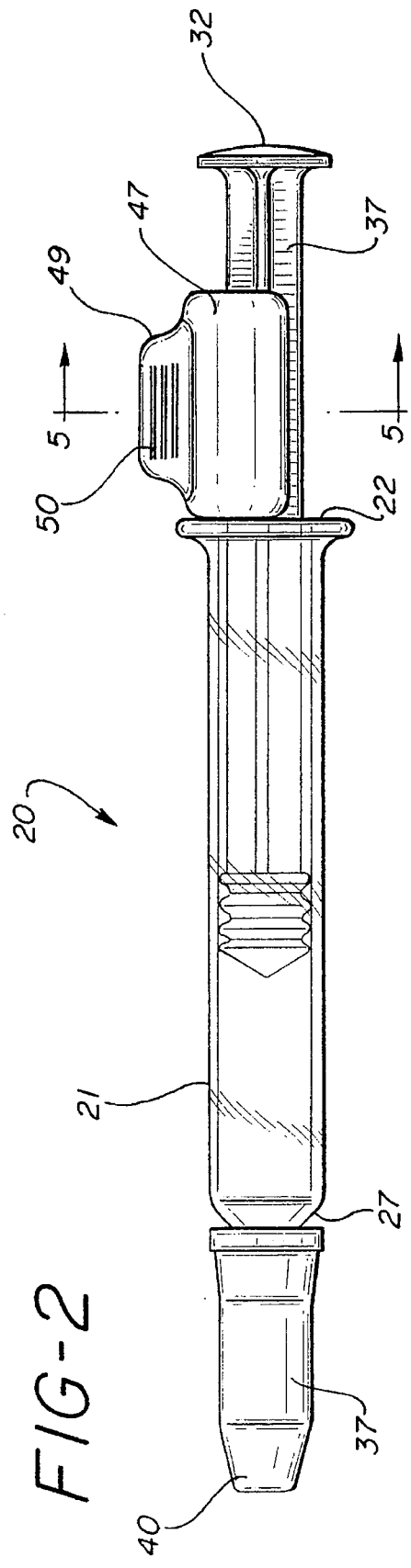
FIG. 2 is a side elevation view of the syringe nasal sprayer of FIG. 1.
Figure 3:
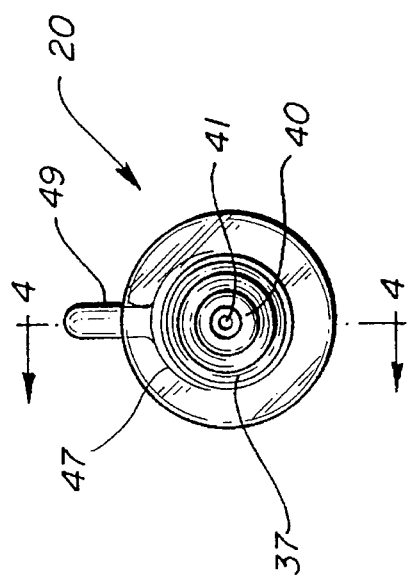
FIG. 3 is a side elevation view of the syringe nasal sprayer of FIG. 1 viewed from the distal end.

While this invention is satisfied by embodiments in many different forms, there is shown in the drawings and will herein be described in detail preferred embodiments of the invention with the understanding that the present disclosure is to be considered exemplary of the principles of the invention and is not intended to limit the invention to the embodiments illustrated. The scope of the invention will be measured by the appended claims and their equivalents.

Adverting to FIGS. 1–7, a syringe nasal sprayer 20 of the present invention comprises an elongate barrel 21 having an open proximal end 22, a chamber 23 for retaining liquid and a tip portion 25 extending from a distal end 27 of the barrel having a passageway 28 therethrough communicating with the chamber.

For the purposes of the description of the present invention, the term "distal end" is meant to refer to the end furthest from the person holding the syringe nasal sprayer whereas the term "proximal end" is meant to refer to the end closest to the holder of the syringe nasal sprayer.

A stopper 29 is slidably positioned in fluid-tight engagement inside barrel 21 and is adopted to engage an elongate plunger rod 31 to facilitate its operation. The plunger rod projects proximally from the stopper and extends outwardly from the open proximal end of the barrel. The plunger rod is accessible outside of the proximal end of the barrel and is provided to move the stopper along the barrel to force liquid out of the chamber through the passageway. Specifically, the stopper is capable of moving liquid from chamber 23 through passageway 28 upon its movement toward distal end 27 of the barrel. In this embodiment, the stopper contains an internal thread (not shown) which engages an external thread (not shown) on the plunger rod. There are numerous other constructions that can be used to join a plunger rod and a stopper such as an interference or snap-fit arrangement or through the use of adhesives. It is also possible to make a one-piece plunger stopper assembly such as by injection molding one or two materials in a mold cavity. The arrangement described hereinabove is exemplary of these many possibilities which are all within the purview of the present invention.

A disc-shaped plunger rod flange 32 is provided on the proximal end of the plunger rod to perform several functions. One such function is that flange 32 is a convenient structure for applying forces to move the plunger rod with respect to the barrel. The large surface area of the flange reduces the pressure on the fingers while delivering medication through the nasal sprayer.

A stopper flange 33 at the distal end of the plunger rod is provided to supply a large surface area to transmit force from the plunger rod to the stopper in a direction toward the stopper, without damaging the stopper. It will be apparent to one skilled in the art that there are numerous constructions that can be used to join a stopper and a plunger rod and that the arrangement described herein is exemplary of these many possibilities. Also, it is within the purview of this invention to include a one-piece plunger rod-stopper assembly.

A therapeutic liquid such as liquid medication 35 is contained within chamber 23. A spray nozzle 37 extends outwardly from the tip portion of the barrel and includes a conduit 39 therethrough in fluid communication with passageway 28. The spray nozzle includes a distal end 40 having a spray aperture 41 in fluid communication with conduit 39.

The spray nozzle of the present invention is different from nozzles in prior art syringes having spray adapters in that the instant spray nozzle includes a means for preventing unpressurized liquid in the chamber from flowing through the spray aperture while allowing liquid under pressure in chamber 23 to flow distally through the conduit and spray aperture 41. This one-way valve feature allows the syringe nasal sprayer of the instant invention to be prefilled by a pharmaceutical manufacturer or in the hospital pharmacy and to be used at a future time or date. The one-way valve feature isolates the contents of the syringe from the environment and eliminates the need for other mechanisms to preclude flow through the distal end of the nasal sprayer.

The spray nozzle of this embodiment comprises two components, a cap 38 and a flexible valve 45. Cap 38 is secured to tip portion 25 of the barrel by virtue of an interference fit between enlarged portion 43 of tip 25 and interior surface 44 of the cap. In this embodiment the interference fit between the barrel, which is preferably made of glass, and the cap, which is preferably plastic, is a preferred way of joining these components. It should be noted that many materials are suitable for the barrel and for the cap and that numerous joining methods such as adhesive, heat sealing, and the like are all within the purview of the instant invention.

Flexible valve 45 is contained within the cap between tip portion 25 and distal end 40 of the cap. Flexible valve 45 interacts with cap 38 to allow liquid under pressure in the chamber to flow distally through spray aperture 41 preventing unpressurized liquid in the chamber from flowing through the aperture. The valve in this preferred embodiment is a skirt valve having a circumferential skirt 46 which will partially collapse under the force of pressurized liquid in the chamber to allow liquid to flow from the chambers through the spray aperture. The skirt collapses by moving away from the side wall of the cap allowing liquid to pass through the liquid pressure created gap between the skirt and the cap.

Spray nozzles are taught in the prior art and are commercially available from numerous manufacturers such as SOFAB of Paris, France. Spray nozzles are taught in SOFAB's French Patent Application No. 2,635,084. The valve and cap assembly of the preferred embodiment is preferably made of two pieces to reduce cost and simplify assembly. The principle of a flexible skirt valve in a rigid housing is embodied in prior art valves such as the SOFAB valve referred to hereinabove.

Another advantage of the spray nozzle of the instant invention is that a certain amount of pressure within chamber 23 is required before the valve will open. Accordingly, when the valve opens (i.e., the skirt collapses), the liquid is pressurized and is propelled past the valve through the spray aperture. If the pressure in the chamber becomes too low the valve will stop the flow of liquid, so that the valve acts as a means for protecting the contents of the syringe during storage and as a regulator to only allow pressurized liquid through the spray aperture. These are important features of the Applicant's syringe nasal sprayer which are not found in prior art nasal spraying devices.

Another important feature and advantage of preferred embodiment of the present invention over the prior art is that it cannot be refilled after use. Accordingly, this invention protects the user from potential infection, contamination or injury caused by refilling, using improper procedures, the wrong drug or in a non-sterile or contaminated environment. The single-use feature or means of the preferred syringe nasal sprayer protects the patient by not allowing additional medication to be drawn into barrel chamber 23 through passageway 28 by placing the spray nozzle in fluid communication with a liquid medication and pulling the plunger in a proximal direction with respect to the barrel to create a sub-atmospheric pressure in the chamber. This method, the most common method of filling a hypodermic syringe, cannot be practiced with the instant invention because flexible valve resists liquid flow in a proximal direction. Flow in the proximal direction is resisted by skirt 46 of flexible valve 45 which expands against the walls of conduit 39 when liquid attempts to move proximally. Also, pressure differentials which tend to force liquid in a proximal direction will force the valve against distal end surface 51 of tip portion 25. To further resist liquid flow in a proximal direction, the valve may be designed with a central projection (not shown) or with a flat proximal or bottom surface so that it will occlude or block passageway 28 when it is subject to forces in a proximal direction.

The syringe of the present invention is intended to be originally filled from the open proximal end of the barrel. The stopper is then inserted using an assembly tool which will allow air to escape while the stopper is being inserted into the barrel. Preferably the stopper can be inserted while the syringe and medication are in an evacuated chamber so that little or no air is trapped in the chamber when the stopper is inserted. A syringe so filled by a pharmaceutical manufacturer or other entity remote from the ultimate user is referred to as a prefilled or prefillable syringe.

Figure 5:
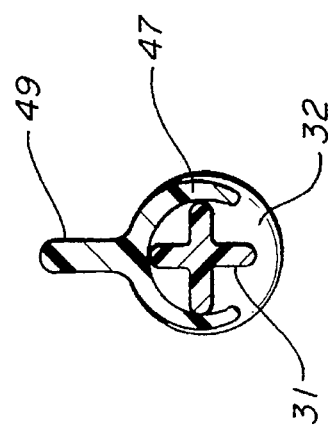
FIG. 5 is a cross-sectional view of the syringe nasal sprayer of FIG. 2 taken along line 5—5.

Another important feature and advantage of the syringe nasal sprayer of the instant invention over the prior art is that it combines the above-mentioned features along with a means for limiting the amount of therapeutic liquid delivered to the patient so that, for example, the dosage may be divided into equal amounts for each nostril. To perform this function, the instant invention preferably includes dosage limiting housing 47 having a C-shaped cross-section, as best illustrated in FIG. 5. Housing 47 partially surrounds the plunger rod so that the housing will not fall off the plunger rod under its own weight but may be forceably removed from the plunger rod without eliminating the ability of the syringe nasal sprayer to deliver medication from the chamber through the aperture. The housing may be designed with a thin cross-section so that it will deflect and snap over the plunger rod or the plunger rod may be designed to deflect under the forces of the housing. Also, both elements may be designed to deflect partially during installation and removal of the housing.

Figure 4:
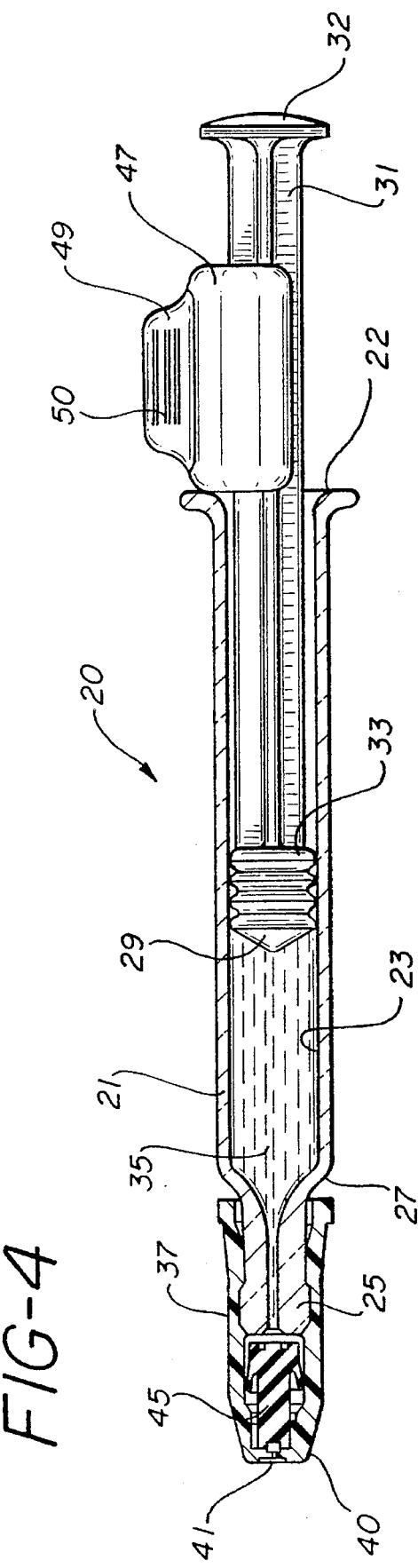
FIG. 4 is a partial cross-sectional view of the syringe nasal sprayer of FIG. 3 taken along line 4—4.
Figure 6:
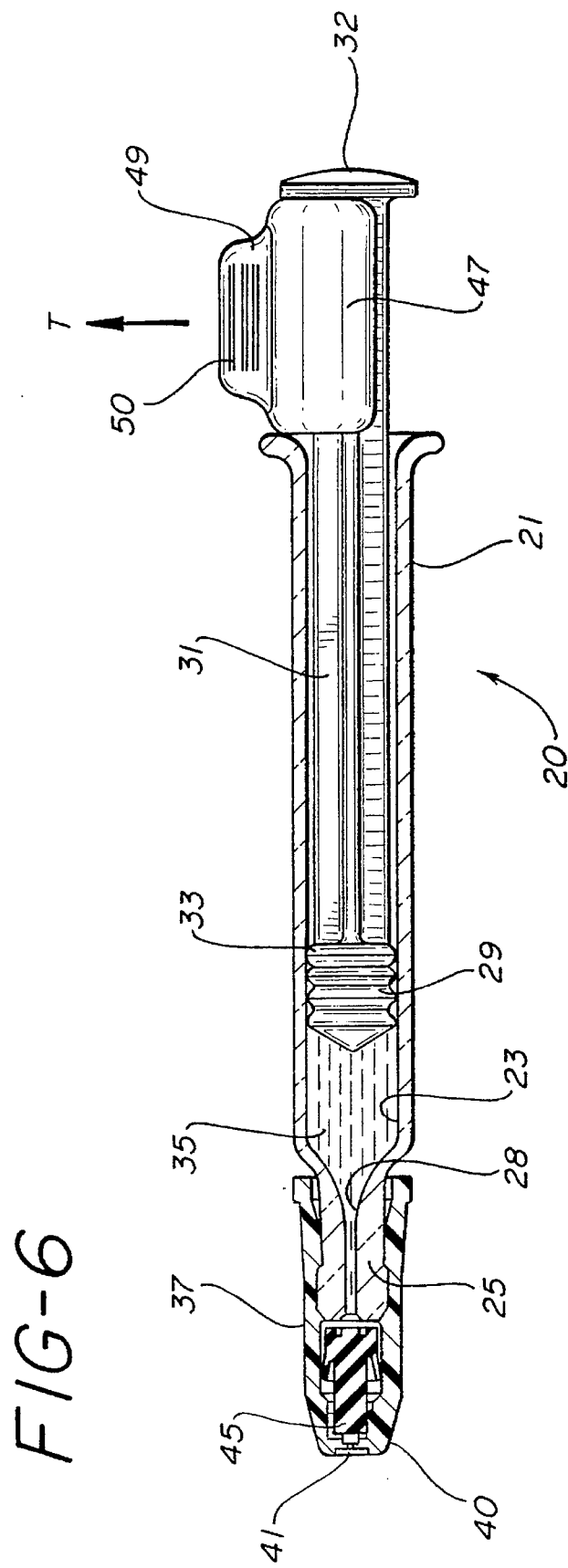
FIG. 6 is a partial cross-sectional view, similar to the partial cross-sectional view of FIG. 4, illustrating the syringe nasal sprayer after one-half of the medication has been delivered.

Housing 47 is adapted to interact between a radially extending projection on the plunger rod such as flange 32 and proximal end 22 of the barrel which includes a barrel flange 26 to limit the distal motion of the plunger rod with respect to the barrel. For example, the length of housing 47 can correspond to one-half of the volume of therapeutic liquid in chamber 23. In use, the syringe nasal sprayer can be inserted into one nostril of the patient while it is fully loaded as best illustrated in FIG. 4. Pressure on the plunger rod flange in a distal direction will cause therapeutic liquid to flow through the passageway into conduit 39 of the cap, deflecting the skirt portion 46 of the flexible valve, and through spray aperture 41. The plunger rod will move until its further distal motion is prevented by contact of the plunger rod flange 32 with housing 47 which in turn contacts barrel flange 26. The plunger rod can no longer be moved in a distal direction and approximately one-half of the therapeutic liquid still remains in the syringe. To continue to therapy, the user removes the syringe nasal sprayer from the one nostril. The user then pulls the housing in direction T, as illustrated in FIG. 6 to remove the housing from the plunger rod. To facilitate the removal of housing 47 from the plunger rod a finger tab portion 49 is provided. In this preferred embodiment, finger tab 49 includes ribs 50 on both sides of the finger tab to facilitate gripping the tab. The tab once so gripped can be pulled in direction T to remove the housing from the plunger rod.

With the housing removed, the syringe nasal sprayer may now be placed so that the spray nozzle is in the other nostril of the patient and the remaining half of the therapeutical liquid may be delivered. The dosage limiting housing of the present invention is an important advantage of the instant syringe nasal sprayer over prior art devices. The housing does not necessarily have to divide the dose into one half portions but can be sized to facilitate any sequence which is therapeutically useful for two subsequent doses.

A housing can also be provided which is equivalent to the full dose of therapeutic liquid in the chamber so that it is impossible to deliver any therapeutic liquid until the housing is removed. This feature is desirable if the syringe nasal sprayer will be subject to extreme forces and conditions between filling and time of use because it physically prevents the forward distal motion of the plunger rod with respect to the barrel until time of use. Multiple housings can also be provided. For example, two housings, each sized to prevent delivery of one-half of the dose can be provided so that the syringe nasal sprayer will be protected from forces which could move the plunger rod during shipping and will be able to deliver two approximately equal doses of therapeutic liquid at the time of use.

The instant invention can be used in any medical application where medication or therapeutic liquid in a spray form is required such as for spraying liquid onto the eye or into an open wound or onto an irritated area such as a burn, and the nasal application described herein is exemplary of these many uses.

Referring now to FIGS. 8–10 wherein an alternative syringe nasal sprayer 55 is illustrated. In this embodiment the structure of the syringe nasal sprayer is substantially similar to the syringe nasal sprayer of the embodiment of FIGS. 1–7. Accordingly, substantially similar components that perform substantially similar functions will be numbered identically to the components of the embodiment of FIGS. 1–7 except a suffix "a" will be used to identify those components in FIGS. 8–10.

In this alternate embodiment, syringe nasal sprayer 55 includes an elongate barrel 21a having an open proximal end 22a, a chamber 23a for retaining fluid and a tip portion 25a extending from a distal end 27a of the barrel having a passageway 28a therethrough communicating with the chamber.

A stopper 29a is slidably positioned in fluid-tight engagement inside the barrel, an elongate plunger rod 31a projects proximally from the stopper and extends outwardly from the open proximal end of the barrel.

A spray nozzle 37a extends outwardly from the tip portion of the barrel and includes a conduit therethrough. The spray nozzle includes a cap 38a and a flexible valve 45a. The distal end of the cap includes a spray aperture 41a in fluid communication with conduit 39a. Internally positioned flexible valve 45a allows liquid under pressure in the chamber to flow distally through the conduit and through the aperture while preventing unpressurized liquid in the chamber from flowing the aperture. In this embodiment cap portion 38a is integrally formed with tip portion 25a to produce an integral cap-tip member thus eliminating another component. In this embodiment, as illustrated in FIGS. 8–10, the barrel, the tip portion and the cap portion are all one-piece so that the barrel and flexible valve comprise two pieces.

This embodiment includes means for holding the flexible valve in the cap portion so that sub-atmospheric pressure in chamber 23a will not pull the valve back into the chamber. In this embodiment two opposed projections 58 and 59 are formed inside the passageway to prevent withdrawal of the flexible valve from its distal position. Different means may be employed to position the valve depending on the materials and the valve design employed. These means include adhesive, ultrasonic welding and the like.

In use the syringe nasal sprayer of the alternative embodiment of FIGS. 8–10 functions in the same manner to deliver a therapeutic liquid as does the embodiment of the syringe nasal sprayer of FIGS. 1–7.

The barrel of the present invention may be constructed of a wide variety of rigid materials such as metals, plastics, ceramics. Glass is preferred due to its long moisture vapor transmission rate and compatibility with many medication formulations.

A wide variety of rigid materials are suitable for formation of the cap, plunger rod and housing. These materials includes metals or plastic with injection molded plastic being preferred.

A wide variety of materials such as natural rubber, synthetic rubber, thermoplastic elastomers, thermoplastic and thermosets are suitable for forming the flexible valve with thermoplastic and thermoplastic elastomers being preferred.

A wide variety of materials such as natural rubber, synthetic rubber and thermoplastic elastomers are suitable for forming a stopper with natural rubber and butyl rubber being preferred.

Thus the present invention provides a straight-forward, reliable, easily fabricated syringe sprayer which provides the simplicity, ability to store therapeutic liquids and efficiency of a syringe in a device capable of delivering medication in the form of a spray without the use of complex difficult to use medication wasting adapters and without requiring further assembly at time of use which can lead to contamination and misuse. The present invention includes one-way valve features to prevent refilling the syringe after use. The present invention also provides structure to control the amount of medication delivered to each nostril and to control the total amount of liquid delivered.

What is claimed is:

1. A syringe sprayer comprising:

an elongate barrel having an open proximal end, a chamber for retaining fluid and a tip portion extending from a distal end of said barrel having a passageway therethrough communicating with said chamber;

a stopper slidably positioned in fluid-tight engagement inside said barrel;

an elongate plunger rod projecting proximally from said stopper and extending outwardly from said proximal end of said barrel;

a spray nozzle extending outwardly from said tip portion of said barrel having a conduit therethrough in fluid communication with said passageway, a distal end of said nozzle having a spray aperture in fluid communication with said conduit;

said nozzle including internal valve means for allowing liquid under pressure in said chamber to flow distally through said conduit and said aperture while preventing unpressurized liquid in said chamber from flowing through said aperture; and dose limiting means for preventing delivery of a predetermined amount of liquid in said chamber through said passageway by limiting said distal motion of said plunger rod with respect to said barrel, said dose limiting means also including override means for allowing removal of said dose limiting means from said syringe sprayer and delivery of all of the liquid in said chamber.

2. The syringe sprayer of claim 1 wherein said dose limiting means prevents delivery of approximately one-half of the liquid in said chamber.

3. The syringe sprayer of claim 1 wherein said dose limiting means prevents delivery of approximately all of the liquid in said chamber.

4. The syringe sprayer of claim 1 wherein said plunger rod includes a radially extending projection which interacts with said dose limiting means to prevent further distal motion of said plunger rod with respect to said barrel.

5. The syringe sprayer of claim 4 wherein said projection is a flange on the proximal end of said plunger rod.

6. The syringe sprayer of claim 4 wherein said dose limiting means includes an elongate housing having a C-shaped cross section, said housing partially surrounding said plunger rod so that said housing will not fall off said plunger rod under its own weight but may be forceably removed from said plunger rod without eliminating the ability of said syringe sprayer to deliver medication from said chamber through said aperture, said housing adapted to interact with said radially extending projection and said proximal end of said barrel to limit distal motion of said plunger rod with respect to said barrel.

7. The syringe sprayer of claim 6 wherein said housing includes a finger tab portion extending outwardly therefrom, said tab including opposed sides for use as gripping surfaces for applying force to remove said dose limiting means from said plunger rod.

8. A syringe sprayer comprising:

an elongate barrel having an open proximal end, a chamber for retaining liquid and a tip portion extending from a distal end of said barrel having a passageway therethrough communicating with said chamber;

a stopper slidably positioned in fluid-tight engagement inside said barrel;

an elongate plunger rod projecting proximally from said stopper and extending outwardly from said proximal end of said barrel, said plunger rod including a radially extending flange on the proximal end of said plunger rod;

a spray nozzle extending outwardly from said tip portion of said barrel having a conduit therethrough in fluid communication with said passageway, a distal end of said nozzle having a spray aperture in fluid communication with said conduit;

said nozzle including internal valve means for allowing liquid under pressure in said chamber to flow distally through said conduit and said aperture while preventing unpressurized liquid in said chamber from flowing through said aperture;

said internal valve means including one-way valve means for preventing liquid flow through said conduit in a proximal direction toward said chamber; and dose limiting means for preventing delivery of a predetermined amount of liquid in said chamber through said passageway by limiting the distal motion of said plunger rod with respect to said barrel, said dose limiting means also including override means for allowing removal of said dose limiting means from said syringe sprayer and delivery of all of the liquid in said chamber.

9. The syringe sprayer of claim 8 wherein said dose limiting means includes an elongate housing having a C-shaped cross section, said housing partially surrounding said plunger rod so that said housing will not fall off said plunger rod under its own weight but may be forceably removed from said plunger rod without eliminating the ability of said syringe sprayer to deliver liquid from said chamber through said aperture, said housing adapted to interact with said flange and said proximal end of said barrel to limit distal motion of said plunger rod with respect to said barrel.

10. The syringe sprayer of claim 8 wherein said dose limiting means prevents delivery of approximately one-half of the liquid in said chamber.

11. The syringe sprayer of claim 8 wherein said dose limiting means prevents delivery of approximately all of the liquid in said chamber.

12. The syringe sprayer of claim 8 wherein said housing includes a finger tab portion extending outwardly therefrom, said tab including opposed sides for use as gripping surfaces for applying force to remove said dose limiting means from said plunger rod.

13. The syringe sprayer of claim 8 wherein said chamber contains a therapeutic liquid.

\* \* \* \* \*